United States Patent
Morris et al.

(10) Patent No.: US 7,041,169 B2
(45) Date of Patent: *May 9, 2006

(54) METHODS OF GENERATING AND SCREENING FOR HIGH FREE ENERGY FORMS IN CAPILLARIES

(75) Inventors: Kenneth R. Morris, West Lafayette, IN (US); G. Patrick Stahly, West Lafayette, IN (US)

(73) Assignees: S.S.C.I., Inc., West Lafayette, IN (US); Purdue Research Foundation, West Lafayette, IN (US)

( * ) Notice: Subject to any disclaimer, the term of this patent is extended or adjusted under 35 U.S.C. 154(b) by 136 days.

This patent is subject to a terminal disclaimer.

(21) Appl. No.: 10/688,123

(22) Filed: Oct. 17, 2003

(65) Prior Publication Data

US 2004/0139909 A1    Jul. 22, 2004

Related U.S. Application Data

(63) Continuation of application No. 09/752,788, filed on Dec. 28, 2000, now Pat. No. 6,642,060.

(51) Int. Cl.
*C30B 7/14*    (2006.01)

(52) U.S. Cl. .......................... 117/68; 117/69; 436/174; 436/177; 422/245.1

(58) Field of Classification Search ................ 117/68, 117/69; 436/174, 177; 422/245.1
See application file for complete search history.

(56) References Cited

U.S. PATENT DOCUMENTS 6,642,060 B1 * 11/2003 Morris et al. ............... 436/174

* cited by examiner

*Primary Examiner*—Robert Kunemund
(74) *Attorney, Agent, or Firm*—McAndrews, Held & Malloy, Ltd.

(57) ABSTRACT

A method for generating and isolating a high free energy form of a compound or a mixture of compounds comprises the steps of placing a sample in a capillary tube, solidifying the sample in the capillary tube, and isolating a high free energy form of the sample. A method for searching for a high free energy form of a sample comprises the steps of placing the compound or mixture in a capillary tube, generating a solid in the capillary tube, and determining whether a high free energy form of the sample was generated. The sample may be a compound or mixture.

35 Claims, 1 Drawing Sheet

METHODS OF GENERATING AND SCREENING FOR HIGH FREE ENERGY FORMS IN CAPILLARIES

This application is a continuation of Ser. No. 09/752,788, filed on Dec. 28, 2000, now U.S. Pat. No. 6,642,060.

FIELD OF THE INVENTION

The present methods relate to screening and generating high free energy forms from a sample comprising a compound, an element, or a mixture. More particularly, samples are solidified in capillary tubes, and a distribution of solid forms is generated, including high free energy forms. The generated forms may be more stable within the capillary tubes and may be isolated and analyzed within the capillary tubes. The present methods provide an economical and relatively easy way to see whether a compound, element or mixture thereof has a high free energy form.

BACKGROUND OF THE INVENTION

A chemical compound, or a mixture of compounds, may exist in different solid forms, each of which has a characteristic free energy at a given temperature. A compound is a substance composed of atoms or ions in chemical combination. A compound will usually include atoms or ions of two or more elements, but as used herein, may include substances composed of one element. The "form" of a compound or mixture refers to its arrangement of molecules or atoms in the solid or semi-solid state. Different forms of a compound or mixture may be distinguished by their x-ray diffraction patterns as well as other suitable means. A compound or mixture may be arranged in a crystalline state, where the molecules exist in fixed conformations and are arranged in a regular way. A compound or mixture may exist in different possible crystalline forms. Further, a compound or mixture may have different crystalline forms that correspond to different free energy levels. A chemical compound or mixture may be amorphous, meaning that it is not characterized by a regular arrangement of molecules, which tends to indicate a relatively high free energy state. The same compound or mixture may exhibit different properties depending upon which form it is in (such as amorphous or crystalline, or such as one of several different crystalline forms).

A compound or mixture will have a most stable solid form at a given temperature (that is, its lowest free energy form at that temperature), and may have less stable forms, which are referred to herein as high free energy forms, or as metastable forms in some contexts. For example, if a compound crystallizes in a stable crystal form that is the most stable form that can be found, then any other form that is found may be considered a high free energy form, in that it has higher free energy than the most stable form. Such forms are metastable thermodynamically in that they are stable enough to be found in solid form, at least for some period of time.

Past attempts to generate high free energy forms involved flash evaporations, cooling under different conditions, and/or the addition of seeds of solid material. However, some materials strongly resist the generation of high free energy forms, and previous attempts to generate high free energy forms of such materials have not been satisfactory. For example, some systems, such as glycogen, do not form high free energy forms unless there is a change in pH or temperature. However, for a variety of reasons, it may not be desirable to alter pH, temperature or other conditions when attempting to generate high free energy forms.

When a compound has different solid or crystalline forms, the different forms are frequently referred to as polymorphs of the compound. A "polymorphic" compound as used herein means a compound having more than one solid form. For example, a polymorphic compound may have different forms of its crystalline structure, or different forms based upon hydration, or it may have a crystalline form and an amorphous form.

There are several reasons why it may be desirable to search for different polymorph forms, including different free energy forms, of a compound or mixture. Different free energy forms of the same compound or mixture may exhibit different properties. As a result, different free energy forms, including different crystalline forms, of a compound or mixture may have greater or lesser efficacy for a particular application.

One or more solid forms may be generated by crystallization of the sample. Among the phenomena in crystallization are nucleation and growth. Crystal nucleation is the formation of an ordered solid phase from liquids, supersaturated solutions, saturated vapors, or amorphous phases. Crystals may originate on a minute trace of a foreign substance (either impurities or container walls) acting as a nucleation site. Since nucleation may set the character of the crystallization process, the identity of the foreign substance is an important parameter. The presence of "seeds" of other crystalline compounds in a crystallization environment can be beneficial, detrimental, or both, but in any event, usually has an influence. Growth is the enlargement of crystals caused by deposition of molecules on an existing surface.

Typically, a solid to be crystallized is present in a solution at, above, or below its saturation point at a given temperature. Crystallization is initiated or facilitated by removing solvent, changing temperature, and/or adding an antisolvent. The solvent may be removed by evaporation or other means. Alternatively, the temperature of the solution is changed, resulting in crystallization. Eventually the solution reaches a point where crystals will grow.

During a crystallization process, a specific chemical substance may crystallize into different forms. For example, ammonium nitrate exhibits different crystal forms depending on the temperature. Below −18° C., ammonium nitrate exhibits a tetragonal crystal form, and above that temperature, it exhibits an orthorhombic form. Above 32.3° C., ammonium nitrate exhibits a different type of orthorhombic form, and above 84.2° C. it exhibits a trigonal form. Above 125.2° C., ammonium nitrate exhibits a cubic crystal form, and at 169.6° C. ammonium nitrate will liquefy at atmospheric pressure. At a given temperature the lowest free energy form frequently is preferentially formed and the others have relatively higher free energy. Transitions from one polymorph form, pseudopolymorph form, or amorphous form to another form may be accompanied by other physical or chemical changes. The different forms of ammonium nitrate arise from the different packing arrangements into which the molecules crystallize at different temperatures. Some compounds may have different colors that indicate different free energy forms. For example, the compound 5-methyl-2-[(2-nitrophenyl)amino]-3-thiophenecarbonitrile exhibits different colors depending on which solid form it is in.

A specific solid form may be more preferable than another solid form. For example, one polymorph may have a more desirable color or greater hardness or disperse in water more easily than another polymorph. Often one polymorph form is more stable than another form. For example, at 80° C., one orthorhombic form of ammonium nitrate is more stable than the trigonal form. One approach to keeping a less stable polymorph from transforming to a more stable but less desirable polymorph form requires the use of an additive to block rearrangement of the crystal structure leading to the undesired form.

It is known to generate crystalline samples in capillary tubes. For example, U.S. Pat. No. 5,997,636 discusses a method for growing crystals within a capillary tube. The patent primarily discloses crystallizing proteins, and the patent does not disclose the relative free energy of the proteins formed or that different forms of proteins were formed.

As another example, D. Amaro-González et al., "Gas Antisolvent Crystallization Of Organic Salts From Aqueous Solution", Journal Of Supercritical Fluids, 17 (2000) 249–258, discloses results of crystallization of lobenzarit, including crystallizations in capillaries. Lobenzarit is an anti-arthritic agent. Amaro-González et al. state that particle size and agglomeration varied depending on the size of the capillary, that it is shown that the size distribution and morphology can be controlled using different capillary diameters, and that it is possible to obtain individual crystals without agglomeration.

The reference does not disclose that different crystal forms (arrangements at the molecular or atomic level in the solid) were produced. A different particle size or shape does not imply a different crystal form since a solid form can crystallize into many different shapes. For example, snowflakes may comprise a single crystal form having many different crystal shapes. The reference also does not disclose that a plurality of different forms may be generated in a plurality of capillary tubes having the same size and shape.

As another example, U.S. Pat. No. 4,290,835 discloses that various processes are known for growing crystalline bodies and that one such process, referred to as the "capillary die process," generally uses a capillary die or forming member from which the crystalline body can be grown.

As yet another example, U.S. Pat. No. 4,295,857 discusses a process of the crystalline precipitation of a chromogen within a capillary. A chromogen is an aromatic compound having a chemical grouping, the chromophore, which gives color to the compound. The patent discloses that it is desirable to prepare a reagent component or mixture in a capillary because it allows for handling of very small amounts of substance and it excludes or at least reduces the danger of errors in dosing of the substance, such as in clinical chemical applications. The examples disclosed the crystallization of 4-aminophenazone in numerous capillary tubes, such as in wheels of five to ten capillary tubes.

As a final example, U.S. Pat. No. 5,363,797 discloses a method for producing a single organic crystal in a capillary tube.

None of the foregoing references disclose that a high free energy form of a compound or mixture may be obtained by solidification or crystallization within a capillary tube. Indeed, none of those references are directed to generating or searching for different free energy forms of a compound or mixture, and none disclose that a high free energy form may be isolated, analyzed and/or stabilized within a capillary tube.

There are several factors that discourage the use of capillary tubes for solidifying compounds or mixtures. One factor is that capillary tubes are more difficult to work with than other containers. Another factor is that there has been no general recognition that the use of capillary tubes may affect reactions or lead to compositional or chemical differences. Thus, since it was believed that the same forms and reactions could be done in other containers, it is believed that capillary tubes have not been used to search for and generate high free energy forms.

SUMMARY OF THE INVENTION

As one aspect, a method of generating a high free energy form of a sample is provided. The method comprises the steps of disposing a sample in at least one capillary tube, solidifying the sample in the capillary tube(s), and isolating at least one high free energy form of the sample.

The solidifying step can comprise crystallizing the sample, using solvent evaporation or antisolvent addition, gel diffusion, and thin-layer deposition. Alternatively, change in temperature can be used to crystallize the sample.

The method may further comprise the step of preparing the sample from a supersaturated solution of at least one compound.

It has been discovered that an isolated high free energy form is readily stabilized within the capillary tube and further efforts at stabilization may not be necessary. Indeed, in many cases, the high energy form is sufficiently stable within the capillary tube for at least 24 hours. The method may further comprise the step of stabilizing the high free energy form, such as by adding a stabilizing agent or subjecting the form to stabilizing conditions. More preferably, the stabilizing step consists essentially of maintaining the high free energy form of the sample in the capillary tube, without adding a stabilizing agent or subjecting the form to stabilizing conditions.

The method may further comprise the step of identifying the high free energy form by a method selected from the group consisting of visual analysis, microscopic analysis, thermal analysis, diffraction analysis, and spectroscopic analysis.

As another aspect, a method of searching for a high free energy form of a sample is provided. The method comprises the steps of disposing a sample in a capillary tube, solidifying the sample in the capillary tube, and determining whether a high free energy form of the sample is in the capillary tube.

In the present methods, the sample may be placed in at least five capillary tubes, alternatively at least 10 capillary tubes. The sample may be placed in at least two sets of capillary tubes, and at least one set differs from at least one other set. For example, the capillary tubes of at least one set may have a different inner diameter than the capillary tubes of at least one other set. The sample may be placed in at least four sets of capillary tubes, and each set may differ from the other sets with respect to the size or surface of the capillary tubes within the sets. In some cases, it is advantageous to use at least one capillary tube coated with heparin on the interior of the tube.

The step of determining whether a high free energy form was generated can comprise an analytical method selected from the group consisting of visual analysis, microscopic analysis, thermal analysis, diffraction analysis, and spectroscopic analysis.

Depending on the sample, visual analysis of said form may be sufficient and is relatively quick and easy. In some cases, the determination of whether a high free energy form was generated will comprise generating data indicative of the form or the relative free energy of the generated form and comparing that data to similar data relating to a known form.

DETAILED DESCRIPTION OF DRAWINGS AND PREFERRED EMBODIMENTS

Figure 1:
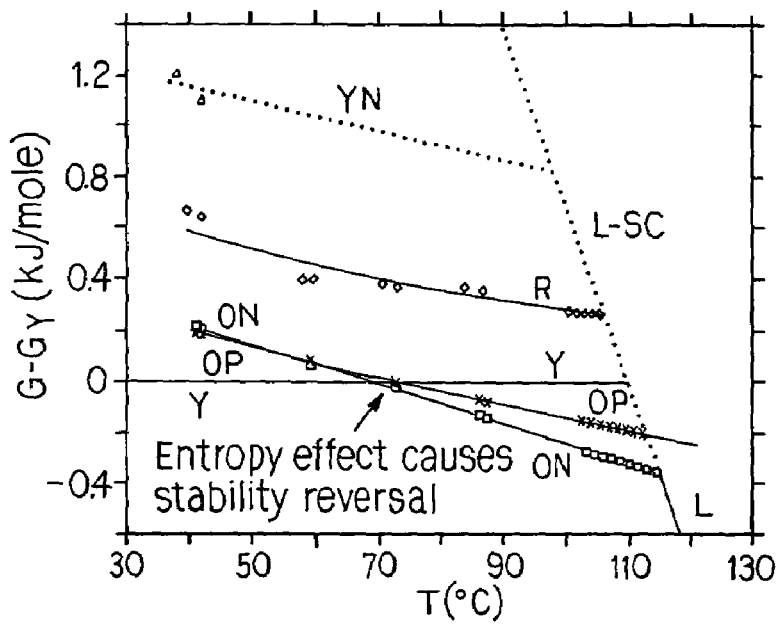
FIG. 1 is an energy-temperature diagram showing the relative thermodynamic stabilities of the various forms of 5-methyl-2-[(2-nitrophenyl)amino]-3-thiophenecarbonitrile.

The present methods relate to searching for and generating high free energy forms of a compound or mixture of compounds by generating solid forms or semisolid forms in one or more capillary tubes. The sample may comprise one compound, an element, a mixture of compound(s), a solution, a suspension, or a dispersion of compound(s) or other material.

A "semisolid" form is used herein to indicate materials like waxes, suspensions, gels, creams, and ointments. The term "solid form" is used herein to also indicate semisolid forms as well. As used herein, the term "compound" may include elemental compounds, the term "molecule" includes collections of atoms, and the term "polymorph" includes allotropes, which are forms based on arrangements of atoms. As used herein, solidifying and solidification include but are not limited to crystallizing and crystallization. As used herein, isolating a high free energy form simply means obtaining it for a sufficient time so that it could be identified, analyzed, or otherwise utilized. The high free energy form need not be isolated in totally pure form; it can be mixed with one or more other forms, so long as it is distinguishable physically, chemical or analytically.

As mentioned above, the step of solidifying the sample may include but is not limited to crystallizing the sample. Indeed, the high free energy forms which may be sought or generated may include amorphous forms, mixtures of amorphous forms, eutectic mixtures, mixed crystal forms, solid solutions, co-crystals and other forms.

Nonetheless, in preferred embodiments of the present methods, solid samples are generated in capillary tubes through a suitable means of crystallization. Typically, a solution containing a compound or mixture to be crystallized and a solvent is placed in a capillary tube. The compound or mixture can be present in a solution below, at, or above its saturation point at a given temperature at the time it is placed in the capillary tube. The concentration of the compound or mixture is increased, through evaporation of the solvent, the use of an antisolvent, or other suitable means, eventually to a concentration where crystallization begins. After a suitable amount of time, when solid or semisolid appears, the resulting sample is ready for analysis, such as diffraction analysis. Alternatively, the solution is cooled or heated so that crystallization occurs.

Suitable capillary tubes tend to include an enclosed space measuring 0.1 mm to about 20 mm, preferably from about 0.5 mm to about 5 mm, most preferably from about 0.5 mm to about 2.5 mm, in at least one dimension. It is preferred that the capillary tubes are circular in their interior shapes and have an inner diameter from about 0.1 mm to about 5 mm, more preferably from about 0.5 mm to about 2.5 mm. The inner diameters of commercially available capillary tubes are sometimes stated as ranges, such as 1.5–1.8 mm, and it is preferred that the stated range fall partially or wholly within one of the preferred ranges described above. Presently preferred capillary tubes are exemplified in the examples below.

Any suitable crystallization technique may be employed for obtaining crystals. For example, crystals may be obtained through cooling, heating, evaporation, addition of an antisolvent, reactive crystallization, and using supercritical fluids as solvents. Additionally, melt crystallization techniques may be used to generate a solid or semisolid. Through such techniques, the use of a solvent can be avoided. In such techniques, formation of crystalline material is from a melt of the crystallizing species rather than a solution. Additionally, the crystallization process may be done through sublimation techniques.

Nucleation and growth of a crystal normally occur after the concentration of the material to be crystallized in solution has reached supersaturation. The concentration may increase as a result of evaporation of the solvent, addition of antisolvent, or absorption of the solvent by another material.

In the present methods, crystallization may be performed as a seeded operation or an unseeded operation. In a seeded operation, a selected quantity of seed crystals is included in the system. The seed crystals may be a high free energy form, which will further encourage the generation of high free energy forms. The characteristics of the seed crystals typically influence the characteristics of the crystals generated from the system. Crystallization may be performed by heterogeneous or homogeneous mechanisms.

In other embodiments of the present methods, the sample is solidified other than by crystallization. The sample may be in the form of a melt which is then added to the capillary tube and allowed to solidify in an amorphous form.

Alternatively, the mechanism by which solidification is accomplished may include gel diffusion methods, thin-layer (with or without subsequent measures to quickly remove residual solvent, including air of various temperatures forced through the capillaries) deposition methods, or other suitable methods. Other thermodynamic and kinetic conditions may be employed to solidify the compound or mixture. Cooling of a saturated solution is a typical thermodynamic condition. An addition of a solution of the compound or mixture to an excess of antisolvent is a typical kinetic condition.

As a further aspect, it has been found that if the capillary tube is held motionless and the material therein is at a suitably high level of supersaturation, there is an advantage for finding high free energy forms.

It may be desirable to determine which solid form is the most stable. Furthermore, relative stability among the various forms can be placed in order either qualitatively or quantitatively. However, these stability orders may differ under different conditions, as the thermodynamic relationship of forms is dependent upon the temperature and pressure conditions under which the sample generations were carried out.

The high free energy forms may be identified by any suitable method, including but not limited to visual analysis (such as when different forms exhibit different colors), microscopic analysis including electron microscopy, thermal analysis such as determining the melting points, x-ray diffraction analysis, infrared spectroscopic analysis, or other spectroscopic analysis. Any appropriate analytical technique that is used to differentiate structural, energetic, or performance characteristics may be used in connection with the present methods. From the analyses, data indicative of the relative free energy of the forms may be obtained and used to identify whether a high free energy form was generated.

This data may be compared to other data generated or to pre-existing data for a known form.

Preferably, the method comprises generating more than one solid form such that a distribution of solid forms is created. From such a distribution, one may determine the frequency of higher versus lower energy forms, and the number of occurrences of them. It is expected that a distribution will typically be heavily skewed towards low free energy forms unless one alters conditions to skew the distribution toward high free energy forms. For example, one may undertake a number of crystallizations of a given compound or mixture and can obtain both low and high free energy forms. In order to obtain a suitable distribution, one should put the sample into a suitable number of individual capillary tubes, for example, five or more capillary tubes, alternatively 50 or more capillary tubes.

However, by generating solid forms in capillary tubes, one may favor the formation of high free energy forms. While the inventors do not wish to be bound by theory, it is believed that capillary tubes may not offer the opportunity for early nucleation, thereby favoring the formation of high free energy forms, and once a high free energy form is crystallized, its transformation into a low energy form will be inhibited by the low perturbation conditions within the capillary tube. Thus, the use of capillary tubes skews the distribution towards less probable high free energy forms without eliminating the formation of low free energy forms. In fact, it is likely that one may still get a majority of low free energy forms.

Again, while the inventors do not wish to be bound by theory, it is presently hypothesized that the use of a capillary tube is advantageous in generating high free energy forms because one can maintain a higher level of supersaturation within the capillary tube, thereby reducing the tendency for premature solidification as a low free energy form. Also, it is presently believed that the dimensions and possibly curved shape of the capillary tubes promote generation of unusually high free energy forms. Furthermore, the capillary tube may provide a way of matching dimensions between the crystal structures and the medium. Regardless of the correctness of any theory, the use of capillary tubes has been empirically demonstrated to be a successful method of generating high free energy forms of certain compounds, as shown in the following examples.

EXAMPLE 1

For this example, the compound 5-methyl-2-[(2-nitrophenyl)amino]-3-thiophenecarbonitrile was used. This compound has conformational forms having three different colors: Red, Orange and Yellow. In view of this variety of colors, the compound has been referred to as "ROY". There are six known conformational polymorph forms in which ROY may exist. FIG. 1 is an energy-temperature diagram showing the relative thermodynamic stabilities of the various forms of the ROY compound. As indicated in FIG. 1, the form indicated by yellow needles is the least stable (that is, it is the highest free energy form shown) at room temperature. In FIG. 1, "YN" indicates yellow needles, "R" indicates the red form, "ON" indicates orange needles, "OP" indicates orange plates, and "Y" indicates yellow. "L" demarcates the conditions beyond which the compound will be in liquid form.

For this example, a solution of ROY in ethanol was prepared. A supersaturated solution of 160.3 mg of ROY in 2 mL of ethanol was prepared, having a supersaturation ratio of 6.7. The ROY compound has solubility in ethanol of approximately 12 mg/mL at 25 degrees C.

Two sets of capillary tubes were used in this example, and each set included five capillary tubes. The first set were open-ended Kimox-51 capillary tubes having a stated inner diameter of 1.5–1.8 mm. The second set were open-ended capillary tubes having a stated inner diameter of 0.5–0.6 mm. When the smaller capillary tubes were initially received from the supplier, they were coated with heparin. In this example, the smaller tubes were "washed" by soaking them in distilled water for about 10 minutes, rinsing with ethanol, and drying in an oven at 65 degrees C. for at least one hour.

The ROY/ethanol solution was introduced to each capillary tube by capillary action, and then the solution was poured out the opposite end. This was to remove all but a thin layer of solution clinging to the walls of the capillary. Both ends of the capillary tubes were open and free of plugs.

In some instances with larger capillary tubes, one end became plugged with ROY crystals, and the plugged end was broken off so that the end was open. In the smaller capillary tubes, the residual remaining in the tubes was found mostly as small droplets on the interior surface of the tubes, although some residual was found as plugs in the capillary. The capillary tubes were allowed to sit for several hours at room temperature.

After solidification, the following results were seen. In the larger capillary tubes, high free energy yellow needles formed, with red plates forming later among the yellow needles. However, a majority of the high free energy yellow needles remained. In the smaller capillary tubes, approximately one-half of the small droplets crystallized, initially displaying high free energy yellow needles, which eventually converted to orange needles. The small droplets were red in color, and the residual plugs were yellow.

This example indicates that high free energy forms may be obtained by solidification in capillary tubes. The highest free energy form known for the ROY compound was preferentially obtained in capillary tubes of two different sizes by crystallization from a supersaturated solution. Furthermore, the high free energy form yellow needles were sufficiently stabilized in the capillary tubes without other stabilizing efforts, particularly in the larger capillary tubes.

EXAMPLE 2

In this example, the ROY compound was solidified in capillary tubes by a process including the use of water as an anti-solvent. The ROY compound is generally insoluble in water.

Two sets of five capillary tubes were used in this example, the first having a stated inner diameter of 1.5–1.8 mm and the second having a stated inner diameter of 0.5–0.6 mm. The capillary tubes all contained water toward one end of the tubes.

Attempts were made to introduce a solution containing 16.5 mg/mL of ROY in ethanol to each of the capillary tubes. The ROY solution was not pulled into the smaller capillary tubes containing water. In the larger capillary tubes, the ROY solution was successfully introduced by capillary action, and an open gap (containing air) was maintained between the ROY solution and the water in the capillary tubes.

The ethanol of the ROY solution evaporated from the open end with the water acting as an anti-solvent to increase the supersaturation. The ROY compound solidified by crystallization in the places from which the ethanol evaporated. In most of the larger capillary tubes, the solids comprised approximately 75% to 90% yellow needles, which are a high free energy form, with the remainder comprising red plates and orange needles. By breaking the capillary tube, it is possible to separate the various forms for separate analyses. This would be useful for single crystal structure determination studies. The capillary tubes were allowed to sit at room temperature, with the effect that more red plates began to appear, at the expense of yellow needles. However, the red plates also constitute a high free energy form, and a significant amount of yellow needles remained.

This example shows that it may be easier to introduce solutions to capillary of certain sizes when relying on capillary action alone. This example also shows that a wide variety of forms may be obtained in a single solidification, as a mixture of forms corresponding to each of the three colors of the ROY compound were obtained.

EXAMPLE 3

This example was performed in a fashion similar to Example 2, except that the ends of the capillary tubes were plugged to prevent evaporation to the atmosphere.

Three larger capillary tubes (having a stated inner diameter of 1.5–1.8 mm) with water as an antisolvent contained therein had the ROY solution of Example 2 introduced by capillary action. An air gap remained between the ROY solution and the water within each capillary tube. Both ends of each tube were plugged with clay.

After approximately one hour, a faint dark red band of solids appeared near the front of the water layer in two of the three capillary tubes. After three days, the red band in the two capillary tubes was slightly fainter but still present, but no band or other solids had formed in the third capillary tube. After six days the faint red band was still present in two tubes and small spots of red appeared near the front of the ROY solution. Microscopic analysis showed no obvious crystalline phase. The significance is that the amorphous form is the highest energy solid form, demonstrating that a high free energy form was generated and stabilized by the method.

EXAMPLE 4

In this example, a supersaturated solution of ROY in ethanol was solidified by evaporation in capillary tubes of different sizes. A large number of solidifications were performed in order to generate a distribution of solid forms, some being high free energy forms.

A supersaturated solution of ROY in ethanol was prepared by mixing approximately 250 mg of the ROY compound in 20 mL of ethanol. The ROY solution was introduced into about 150 capillary tubes having different inner diameters or preparation procedures. More specifically, four sets of capillary tubes were used (with about 10 tubes in each set), the first set being capillary tubes having a stated inner diameter of 1.5–1.8 mm, the second set being capillary tubes having a stated inner diameter of 1.1–1.2 mm, the third set being capillary tubes having a stated inner diameter of 0.5–0.6 mm and used as received from the supplier (that is, coated with heparin), and the fourth set being capillary tubes having a stated inner diameter of 0.5–0.6 mm and which were "washed" by soaking for 10 minutes in distilled water, rinsing with ethanol, and drying for at least an hour at 65 degrees C.

After approximately 20 minutes, the capillary tubes were checked for solid forms and re-checked at intervals. In the first set, the ROY compound crystallized primarily as yellow needles, with a small percentage of capillary tubes containing some orange needles instead of yellow needles. In the second set, a few capillary tubes contained yellow needles exclusively, but most tubes contained a mixture of about 75–90% yellow needles with the remainder of solids comprising red plates. In the third set, all the capillary tubes contained yellow needles. In the fourth set, most of the capillary tubes contained yellow needles with a small amount of red plates mixed in, though a few capillary tubes contained yellow needles exclusively or orange needles exclusively.

In this example, the high free energy form yellow needles were preferentially formed in all four sets of capillary tubes. The 0.5–0.6 mm capillary tubes coated with heparin exclusively produced yellow needles. The washed 0.5–0.6 mm capillary tubes and the 1.1–1.2 mm capillary tubes contained a mixture that included forms corresponding to the color red, while the 1.5–1.8 mm capillary tubes contained a mixture that included forms corresponding to the color orange. This indicates that the use of capillary tubes of different sizes may be desirable in order to obtain a greater variety of high free energy forms.

EXAMPLE 5

Figure 2:
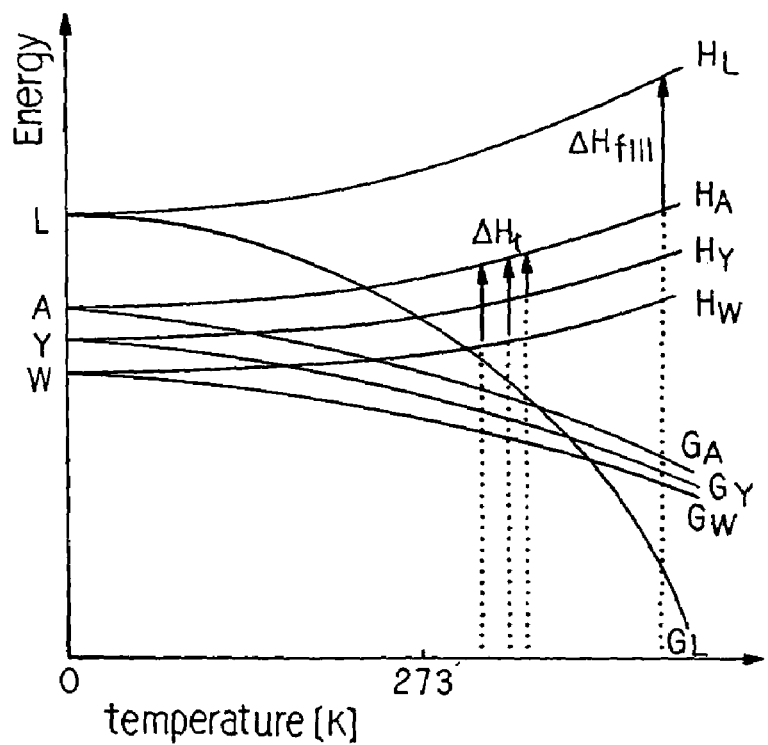
FIG. 2 is an energy-temperature diagram showing the relative thermodynamic stabilities of the various forms of 4-methyl-2-nitro-acetanilide.

For this example, the compound 4-methyl-2-nitro-acetanilide was used. This compound has conformational forms having three different colors: White, Amber and Yellow. In view of this variety of colors, the compound has been referred to as "WAY". FIG. 2 is an energy-temperature diagram showing the relative thermodynamic stabilities of the various forms of the WAY compound. "$H_L$" indicates the enthalpy of the liquid. "$H_A$" indicates the enthalpy of the amber form. "$H_Y$" indicates the enthalpy of the yellow form. "$H_W$" indicates the enthalpy of the white form. "$G_L$" indicates the free energy of the liquid. "$G_A$" indicates the free energy of the amber form. "$G_Y$" indicates the free energy of the yellow form. "$G_W$" indicates the free energy of the white form. The white forms are the most stable, the yellow forms are less stable than the white, and the amber forms are the least stable (that is, they have the highest free energy).

A supersaturated solution of WAY in ethanol was prepared, having a supersaturation ratio of 2. The WAY solution was introduced into 95 capillary tubes. The tubes were left open at both ends and allowed to evaporate to the atmosphere. After about 25 minutes, sixty-two capillary tubes contained crystals. Of these, forty contained white crystals and twenty-two contained yellow crystals. After about one hour, four additional capillary tubes contained white crystals, nine additional capillary tubes contained yellow crystals, and one additional capillary tube contained a mixture of white and yellow crystals. After about 95 minutes, two additional capillary tubes contained white crystals, and seventeen capillary tubes did not yet contain solids.

After waiting overnight (for a total of about thirteen hours and forty minutes after introducing the WAY solution to the capillary tubes), of the remaining seventeen capillary tubes, six contained yellow crystals, three contained a mixture of yellow and white crystals, five contained white crystals, and three did not contain solids. Of the twenty-two capillary tubes that showed yellow crystals after 25 minutes, the crystals in nineteen of those tubes had transformed to white crystals, which reflects the fact that the yellow crystals were less stable and had a higher free energy than the white crystals. However, of the nine capillary tubes that contained yellow crystals after one hour, six still contained yellow crystals after waiting overnight, and one contained a mixture of yellow and white crystals.

These results are significant and unexpected because yellow crystals are relatively less stable at room temperature and readily transform to white crystals. The persistence of yellow crystals overnight while in the solid state is unexpected, and it will facilitate the study of the higher free energy yellow crystals. Furthermore, in this case, slower generation of higher free energy yellow crystals tended to improve the likelihood that those high free energy crystals would last a longer period of time.

Although the example did not generate amber crystals, it is expected that the use of different procedures employing capillary tubes may lead to the generation of amber crystals.

EXAMPLE 6

For this example, solutions of the WAY compound were prepared at a supersaturation ratio of 2 in ethanol and in 10% aqueous ethanol. Each of these WAY solutions was introduced into twenty capillary tubes having a stated inner diameter of 0.5–0.6 mm and which had been washed by soaking in distilled water for about 10 minutes, rinsing with ethanol, and drying for at least an hour at 65 degrees C. The capillary tubes were maintained at room temperature and pressure (about 23 degrees C. and at about 45% relative humidity) and were observed periodically.

Of the capillary tubes containing the WAY/ethanol solution, after about 40 minutes, the solution had evaporated from fourteen of these capillary tubes, and they contained either white crystals or a mixture of white and yellow crystals; after about 20.5 hours, only one tube still did not show any crystallization, and all the other capillary tubes contained yellow crystals or white crystals, with a couple of exceptions.

Of the capillary tubes containing the WAY/aqueous ethanol solution, after one hour, there was no crystallization in any of the capillary tubes; after 21 hours, nine of the twenty capillary tubes did not show any crystallization, but the other eleven contained either yellow crystals or white crystals, with a couple of exceptions.

Solidification of the WAY compound from ethanol and aqueous ethanol solutions was also done at different temperatures (reported below in degrees Celsius). Table 1 summarizes the results of seven sets of twenty capillary tubes under set different sets of conditions.

TABLE 1

| Solvent | Temp | Time | Result |
|---|---|---|---|
| Ethanol | −2 | 4 | 10/20: white crystals<br>2/20: white and yellow crystals |
| Aqueous ethanol | −2 | 4:35 | 19/20: yellow crystals<br>1/20: white crystals |
| Ethanol | 38 | 0:50 | 16/20: mixture of white and yellow crystals, with more white than yellow and with white crystals grown out of end of the capillary tube;<br>4/20: no solids formed |
| Ethanol | 38 | 1:43 | 17/20: mixture of yellow and white crystals;<br>3/20: no solids formed |
| Aqueous ethanol | 38 | 0:50 | 2/20: mixture of yellow and white crystals;<br>18/20: no solids formed |

TABLE 1-continued

| Solvent | Temp | Time | Result |
|---|---|---|---|
| Aqueous ethanol | 38 | 1:13 | 5/20: mixture of yellow and white crystals;<br>15/20: no solids formed |
| Aqueous ethanol | 38 | 1:42 | 19/20: mixture of yellow and while crystals;<br>1/20: no solids formed |

As shown above, all the conditions were at least partly successful in generating high free energy forms, in that all produced at least a mixture of yellow and white crystals. The use of an aqueous ethanol solution at low temperature was particularly successful in generating high free energy forms.

In general, when crystals are generated under similar conditions in a similar timeframe using traditional containers, only white crystals are found.

What is claimed is:

1. A method of generating and screening for one or more high free energy forms of a compound, element or mixture, said method comprising the steps of:
   disposing a non-solid sample of the compound, element or mixture in a plurality of capillary tubes;
   solidifying the sample in the plurality of capillary tubes, whereby a plurality of solids is generated; and
   determining whether one or more high free energy forms were generated using an analytical method selected from the group consisting of visual analysis, microscopic analysis, thermal analysis, diffraction analysis, and spectroscopic analysis.

2. The method of claim 1 wherein the solidifying step comprises crystallizing the sample.

3. The method of claim 1 wherein the solidifying step comprises the use of an antisolvent.

4. The method of claim 1 wherein the solidifying step is selected from the group consisting of solvent evaporation, antisolvent addition, gel diffusion, and thin-layer deposition.

5. The method of claim 1, further comprising the step of preparing the sample from a supersaturated solution of the compound, element or mixture.

6. The method of claim 1, wherein said isolated high free energy form is stabilized within the capillary tube by adding a stabilizing agent.

7. The method of claim 6, wherein said isolated high free energy form is stable within the capillary tube for at least 24 hours.

8. The method of claim 1, further comprising the step of stabilizing the high free energy form for at least 24 hours essentially by maintaining the high free energy form in the capillary tube.

9. The method of claim 1, wherein the sample is placed in at least two sets of capillary tubes, and at least one set differs from at least one other set.

10. The method of claim 9, wherein the capillary tubes of said at least one set have a different inner diameter than the capillary tubes of said at least one other set.

11. The method of claim 9, wherein the sample is placed in at least four sets of capillary tubes, and each set differs from the other set with respect to the size or surface of the capillary tubes within said sets.

12. The method of claim 1, wherein said at least one capillary tube is coated with a substance on the interior of said tube.

13. The method of claim 1, wherein the step of determining whether the high free energy form was generated comprises generating data indicative of the relative free energy of the generated form and comparing said data to data relating to a known form.

14. The method of claim 1 wherein the high energy forms exhibit different colors.

15. The method of claim 1, further comprising identifying the high free energy forms by visual analysis.

16. The method of claim 1 wherein the microscopic analysis is electron microscopy.

17. The method of claim 1 wherein the diffraction analysis is x-ray diffraction.

18. The method of claim 1 wherein the spectroscopic analysis is infrared spectroscopy.

19. The method of claim 1 further comprising analyzing the known solid form to determine the free energy.

20. The method of claim 1, wherein the step of determining whether one or more high free energy forms were generated comprises determining whether a distribution of solid forms occurred.

21. The method of claim 1, wherein the step of determining whether a high free energy form was generated comprises thermal analysis.

22. The method of claim 21 wherein the thermal analysis is determining the melting points.

23. A method of generating and screening for one or more high free energy forms of a compound, element or mixture, said method comprising the steps of:
   disposing a non-solid sample of the compound, element or mixture in a plurality of capillary tubes;
   solidifying the sample in the plurality of capillary tubes, whereby a plurality of generated solids is generated;
   determining whether one or more high free energy forms were generated using an analytical method selected from the group consisting of visual analysis, microscopic analysis, thermal analysis, diffraction analysis, and spectroscopic analysis;
   determining the number of occurrences of each of said solid forms; and
   assigning a relative free energy to each of said solid forms based on the number of occurrences, wherein a high free energy form is associated with a lower number of occurrences.

24. The method of claim 23 wherein the plurality comprises at least 10 capillary tubes.

25. The method of claim 24 wherein the plurality comprises at least 50 or more capillary tubes.

26. The method of claim 25 wherein the plurality comprises at least about 150 capillary tubes.

27. The method of claim 23, wherein the plurality of capillary tubes comprises at least two sets of capillary tubes, and at least one set differs from at least one other set.

28. The method of claim 27, wherein the capillary tubes of said at least one set have a different inner diameter than the capillary tubes of said at least one other set.

29. The method of claim 27, wherein the plurality of capillary tubes comprises at least two four of capillary tubes, and each set differs from the other sets with respect to the size or surface of the capillary tubes within said sets.

30. The method of claim 23, wherein said at least one capillary tube is coated with a substance on the interior of said tube.

31. A method of generating and screening for one or more high free energy forms of a compound, element or mixture, said method comprising the steps of:
   disposing a non-solid sample of the compound, element or mixture in a plurality of capillary tubes;
   solidifying the sample in the plurality of capillary tubes, whereby a plurality of solids is generated; and
   determining whether one or more high free energy forms were generated.

32. The method of claim 31, wherein the step of determining whether a high free energy form was generated comprises visual analysis.

33. The method of claim 31, wherein the step of determining whether a high free energy form was generated comprises microscopic analysis.

34. The method of claim 31, wherein the step of determining whether a high free energy form was generated comprises diffraction analysis.

35. The method of claim 31, wherein the step of determining whether a high free energy form was generated comprises spectroscopic analysis.

* * * * *